United States Patent [19]
Houng et al.

[11] Patent Number: 5,939,075
[45] Date of Patent: Aug. 17, 1999

[54] MUTANTS OF *BRUCELLA MELITENSIS*

[75] Inventors: Huo-shu H. Houng, Burtonsville, Md.; Richard L. Warren, Blue Bell, Pa.

[73] Assignee: The United States of America as represented by the Secretary of the Army, Washington, D.C.

[21] Appl. No.: 08/855,714

[22] Filed: May 8, 1997

Related U.S. Application Data

[63] Continuation-in-part of application No. 08/334,129, Nov. 4, 1994, abandoned.

[51] Int. Cl.$^6$ .......................... A61K 39/02; A01N 63/00; C12P 1/00; C12P 21/06
[52] U.S. Cl. ...................................... 424/252.1; 424/235.1; 424/234.1; 424/184.1; 424/93.1; 424/93.2; 435/41; 435/69.1; 435/172.3; 435/252.3; 435/320.1
[58] Field of Search ............................. 424/235.1, 252.1, 424/184.1, 234.1, 93.1, 93.2; 435/320.1, 252.3, 41, 69.1, 172.3

[56] References Cited

U.S. PATENT DOCUMENTS 4,735,801  4/1988  Stocker ..................................... 424/92

OTHER PUBLICATIONS

Adams, Advances in Brucellosis Research. Chapter 17. pp. 250–276, 1990.
O'Callaghan et al. Injection and Immunity 56:419–423, 1988.
Smith et al. Injection and Immunity 55:2774–2776, 1987.
Houng et al. Abstracts of the 94th General Meeting of ASM. p. 133 Abstract #D–208.
Essenberg Abstract of Grant and Progress Report. #0156434, OKL 01565 Dates Oct. 28, 1991 to Sep. 30, 1996.
Levine et al. J. Clin. Invest. 79:888–902, 1987.

*Primary Examiner*—James C. Housel
*Assistant Examiner*—V. Ryan
*Attorney, Agent, or Firm*—Charles H. Harris; John Francis Moran

[57] ABSTRACT

The vaccines are prepared by isolating the Brucella genes complementing mutations in the purEK genes of *Escherichia coli*, physically mapping, determining the DNA sequence, constructing a defined deletion mutation by polynucleotide chain reaction (PCR), introducing a selectable marker into the deletion, and then selecting a purE mutant in Brucella arising by allelic exchange. The resulting Brucella require purines for growth because they lack the purE gene product that is required for the carboxylation of 5'-phosphoribosyl-5-aminoimidazole.

9 Claims, 11 Drawing Sheets pURE3H: 7.0 kb HindIII insert of
Brucella melitensis in pHC79

Fig. 2

Enzymes : 5 of 515 enzymes (Filtered)
Settings :     Circular, Certain Sites Only, Standard Genetic Code
 Hind III

```
CGATTGGGAAACCATGCACCATGCAGCCGACACATTGGAGGCGCTCGGCATCTCCTTCGACGCACGGATC
├───┼───┼───┼───┼───┼───┼───┼───┼───┼───┼───┼───┼───┼───┼─── 70
GCTAACCCTTTGGTACGTGGTACGTCGGCTGTGTAACCTCCGCGAGCCGTAGAGGAAGCTGCGTGCCTAG

GTTTCCGCCCATCGCACCCCTGACAGGCTGGTCGCCTTCGCCAAGGGGGCGAAACGGGAAGGCTTCAAGG
├───┼───┼───┼───┼───┼───┼───┼───┼───┼───┼───┼───┼───┼───┼─── 140
CAAAGGCGGGTAGCGTGGGGACTGTCCGACCAGCGGAAGCGGTTCCCCCGCTTTGCCCTTCCGAAGTTCC

TCATCATCGCAGGCGCCGGCCGCGCCCACCTGCCCGGCATGGCCGCTGCCATGACACCGCTTCCCGTCTT
├───┼───┼───┼───┼───┼───┼───┼───┼───┼───┼───┼───┼───┼───┼─── 210
AGTAGTAGCGTCCGCGGCCGGCGCGGGTGGACGGGCCGTACCGGCGACGGTACTGTGGCGAAGGGCAGAA
      P  F  S  P  P  P  F  W  R  Y  M  M  K  H  L  P  P  V  L  M  N  G  A
                                   purE TGGCGTTCCAGTTCAATCCAAGGCGCTTTCGGGCCAGGATTCGCTACTCTCCATCGTACAGATGCCAGCG
├───┼───┼───┼───┼───┼───┼───┼───┼───┼───┼───┼───┼───┼───┼─── 280
ACCGCAAGGTCAAGTTAGGTTCCGCGAAAGCCCGGTCCTAAGCGATGAGAGGTAGCATGTCTACGGTCGC
  R  R  R  P  K  A  L  Q  N  A  P  R  T  K  P  D  P  A  R  .  K  M  D
                                   purE GGTATTCCCGTCGGCACTCTCGCCATCGGCCGTGCAGGCGCGGTCAATGCCGCCCTTCTCGCCGCCGCCG
├───┼───┼───┼───┼───┼───┼───┼───┼───┼───┼───┼───┼───┼───┼─── 350
CCATAAGGGCAGCCGTGAGAGCGGTAGCCGGCACGTCCGCGCCAGTTACGGCGGGAAGAGCGGCGGCGGC
  K  T  S  L  K  P  G  S  T  I  G  I  I  G  G  G  Q  L  G  V  C  S  P
                                   purE TTCTGGCGCTATATGATGAAGCACTTGCCGCCCGTCTTGATGAATGGCGCAAGGCGCAGACCGAAAGCGT
├───┼───┼───┼───┼───┼───┼───┼───┼───┼───┼───┼───┼───┼───┼─── 420
AAGACCGCGATATACTACTTCGTGAACGGCGGGCAGAACTACTTACCGCGTTCCGCGTCTGGCTTTCGCA
  W  Q  R  R  A  S  V  M  K  P  .  S  L  S  R  T  R  L  P  G  S  T  G  C
                                   purE
```

Fig.3 (a)

```
TGCAGAACGCCCTCGAACGAAGCCTGATCCGGCGAGGTAGAAAATGGACAAGACATCTCTCAAGCCCGG
ACGTCTTGCGGGGAGCTTGCTTCGGACTAGGCCGCTCCATCTTTTACCTGTTCTGTAGAGAGTTCGGGCC  490

Q  S  P  D  C  R  R  L  .  .  P  E  A  L  A  E  T  C  R  R  F  R  R
                                 purE
              deletion (purE)

CTCCACCATCGGCATTATCGGCCGATTGGGAAACCATGCACCATGCAGCCGACACATTGGAGGCGCTCGG
GAGGTGGTAGCCGTAATAGCCGGCTAACCCTTTGGTACGTGGTACGTCGGCTGTGTAACCTCCGCGAGCC  560

H  H  L  .  I  .  K  C  A  S  Q  R  R  R  Q  A  G  .  N  G  A  C  S
                                 purE
                            deletion (purE)

CATCTCCTTCGACGCACGGATCGTTTCCGCCCATCGCACCCCTGACAGGCTGGTCGCCTTCGCCAAGGGG
GTAGAGGAAGCTGCGTGCCTAGCAAAGGCGGGTAGCGTGGGGACTGTCCGACCAGCGGAAGCGGTTCCCC  630

A  P  A  R  R  T  G  N  L  S  G  P  L  H  R  K  A  V  S  Q  R  K  R
                                 purE
                            deletion (purE)

GCGAAACGGGAAGGCTTCAAGGTCATCATCGCAGGCGCCGGCCGCGCCCACCTGCCCGGCATGGCCGCTG
CGCTTTGCCCTTCCGAAGTTCCAGTAGTAGCGTCCGCGGCCGGCGCGGGTGGACGGGCCGTACCGGCGAC  700 deletion (purE)

Nco I
CCATGACACCGCTTCCCGTCTTTGGCGTTCCAGTTCAATCCAAGGCGCTTTCGGGCCAGGATTCGCTACT
GGTACTGTGGCGAAGGGCAGAAACCGCAAGGTCAAGTTAGGTTCCGCGAAAGCCCGGTCCTAAGCGATGA  770

P  F  S  P  P  P  F  W  R  Y  M  M  K  H  L  P  P  V  L  M
                                 purK
    deletion (purE)
```

Fig. 3 (b)

```
CTCCATCGTACAGATGCCAGCGGGTATTCCCGTCGGCACTCTCGCCATCGGCCGTGCAGGCGCGGTCAAT
                                                                      840
GAGGTAGCATGTCTACGGTCGCCCATAAGGGCAGCCGTGAGAGCGGTAGCCGGCACGTCCGCGCCAGTTA

N  G  A  R  R  R  R  P  K  A  L  Q  N  A  P  R  T  K  P  D  P  A  R  .  K
────────────────────────────── purK ──────────────────────────────

GCCGCCCTTCTCGCCGCCGCCGTTCTGGCGCTATATGATGAAGCACTTGCCGCCCGTCTTGATGAATGGC
                                                                      910
CGGCGGGAAGAGCGGCGGCGGCAAGACCGCGATATACTACTTCGTGAACGGCGGGCAGAACTACTTACCG

M  D  K  T  S  L  K  P  G  S  T  I  G  I  I  G  G  G  Q  L  G  V  C
────────────────────────────── purK ──────────────────────────────

GCAAGGCGCAGACCGAAAGCGTTGCAGAACGCCCCTCGAACGAAGCCTGATCCGGCGAGGTAGAAAATGG
                                                                      980
CGTTCCGCGTCTGGCTTTCGCAACGTCTTGCGGGGAGCTTGCTTCGGACTAGGCCGCTCCATCTTTTACC

S  P  W  Q  R  R  A  S  V  M  K  P  .  S  L  S  R  T  R  L  P  G  S
────────────────────────────── purK ──────────────────────────────

ACAAGACATCTCTCAAGCCCGGCTCCACCATCGGCATTATCGGCCGATTGGGAAACCATGCACCATGCAG
                                                                      1050
TGTTCTGTAGAGAGTTCGGGCCGAGGTGGTAGCCGTAATAGCCGGCTAACCCTTTGGTACGTGGTACGTC

T  G  C  Q  S  P  D  C  R  R  L  .  .  P  E  A  L  A  E  T  C  R  R  F
────────────────────────────── purK ──────────────────────────────

CCGACACATTGGAGGCGCTCGGCATCTCCTTCGACGCACGGATCGTTTCCGCCCATCGCACCCCTGACAG
                                                                      1120
GGCTGTGTAACCTCCGCGAGCCGTAGAGGAAGCTGCGTGCCTAGCAAAGGCGGGTAGCGTGGGGACTGTC

R  R  H  H  L  .  I  .  K  C  A  S  Q  R  R  R  Q  A  G  .  N  G  A
────────────────────────────── purK ──────────────────────────────

GCTGGTCGCCTTCGCCAAGGGGGCGAAACGGGAAGGCTTCAAGGTCATCATCGCAGGCGCCGGCCGCGCC
                                                                      1190
CGACCAGCGGAAGCGGTTCCCCCGCTTTGCCCTTCCGAAGTTCCAGTAGTAGCGTCCGCGGCCGGCGCGG

C  S  A  P  A  R  R  T  G  N  L  S  G  P  L  H  R  K  A  V  S  Q  R
────────────────────────────── purK ──────────────────────────────
```

Fig 3 (c)

```
                                    Nco I
CACCTGCCCGGCATGGCCGCTGCCATGACACCGCTTCCCGTCTTTGGCGTTCCAGTTCAATCCAAGGCGC
┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 1260
GTGGACGGGCCGTACCGGCGACGGTACTGTGGCGAAGGGCAGAAACCGCAAGGTCAAGTTAGGTTCCGCG

K   R   H   .   N   R   A   L   A   A   R   P   S   R   R   R   R   S   G   A   I   .   .   S
 ────────────────────────────────────────── purK ──────────────────────────────────────────
              ┌──────────────── deletion (purK) ────────────────────────────
              ■━━━━━━━━━━━━━━━━━━━━━━━━━━━━━━━━━━━━━━━━━━━━━━━━━━━━━━━━━━━

TTTCGGGCCAGGATTCGCTACTCTCCATCGTACAGATGCCAGCGGGTATTCCCGTCGGCACTCTCGCCAT
┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 1330
AAAGCCCGGTCCTAAGCGATGAGAGGTAGCATGTCTACGGTCGCCCATAAGGGCAGCCGTGAGAGCGGTA

P   F   S   P   P   P   F   W   R   Y   M   M   K   H   L   P   P   V   L   M   N   G   A
 ──────────────────────────────────── purK ────────────────────────────────────
 ─────────────────────────────── deletion (purK) ───────────────────────────────
 ━━━━━━━━━━━━━━━━━━━━━━━━━━━━━━━━━━━━━━━━━━━━━━━━━━━━━━━━━━━━━━━━━━━━━━━━━━━━━━

CGGCCGTGCAGGCGCGGTCAATGCCGCCCTTCTCGCCGCCGCCGTTCTGGCGCTATATGATGAAGCACTT
┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 1400
GCCGGCACGTCCGCGCCAGTTACGGCGGGAAGAGCGGCGGCGGCAAGACCGCGATATACTACTTCGTGAA

P   F   S   P   P   P   F   W   R   Y   M   M   K   H   L   P   P   V   L   M   N   G   A
 ──────────────────────────────────── purK ────────────────────────────────────
 ─────────────────────────────── deletion (purK) ───────────────────────────────
 ━━━━━━━━━━━━━━━━━━━━━━━━━━━━━━━━━━━━━━━━━━━━━━━━━━━━━━━━━━━━━━━━━━━━━━━━━━━━━━

GCCGCCCGTCTTGATGAATGGCGCAAGGCGCAGACCGAAAGCGTTGCAGAACGCCCCTCGAACGAAGCCT
┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 1470
CGGCGGGCAGAACTACTTACCGCGTTCCGCGTCTGGCTTTCGCAACGTCTTGCGGGGAGCTTGCTTCGGA

P   F   S   P   P   P   F   W   R   Y   M   M   K   H   L   P   P   V   L   M   N   G   A   R
 ──────────────────────────────────── purK ────────────────────────────────────
 ·deletion (purK)┐
 ■━━━━━━━━━━━━━━■

GATCCGGCGAGGTAGAAAATGGACAAGACATCTCTCAAGCCCGGCTCCACCATCGGCATTATCGGCCGAT
┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼ 1540
CTAGGCCGCTCCATCTTTTACCTGTTCTGTAGAGAGTTCGGGCCGAGGTGGTAGCCGTAATAGCCGGCTA

P   F   S   P   P   P   F   W   R   Y   M   M   K   H   L   P   P   V   L   M   N   G   A
 ──────────────────────────────────── purK ────────────────────────────────────
```

Fig. 3 (d)

```
TGGGAAACCATGCACCATGCAGCCGACACATTGGAGGCGCTCGGCATCTCCTTCGACGCACGGATCGTTT
+----+----+----+----+----+----+----+----+----+----+----+----+----+----+ 1610
ACCCTTTGGTACGTGGTACGTCGGCTGTGTAACCTCCGCGAGCCGTAGAGGAAGCTGCGTGCCTAGCAAA

P  F  S  P  P  P  P  F  W  R  Y  M  M  K  H  L  P  P  V  L  M  N  G  A
   ─────────────────────────────── purK ───────────────────────────────────

Nco I
                          │
CCGCCCATCGCACCCCTGACAGGCTGGTCGCCTTCGCCAAGGGGGCGAAACGGGAAGGCTTCAAGGTCAT
+----+----+----+----+----+----+----+----+----+----+----+----+----+----+ 1680
GGCGGGTAGCGTGGGGACTGTCCGACCAGCGGAAGCGGTTCCCCCGCTTTGCCCTTCCGAAGTTCCAGTA

P  F  S  P  P  P  P  F  W  R  Y  M  M  K  H  L  P  P  V  L  M  N  G  A  R
   ─────────────────────────────── purK ─────────────────────────────────────

CATCGCAGGCGCCGGCCGCGCCCACCTGCCCGGCATGGCCGCTGCCATGACACCGCTTCCCGTCTTTGGC
+----+----+----+----+----+----+----+----+----+----+----+----+----+----+ 1750
GTAGCGTCCGCGGCCGGCGCGGGTGGACGGGCCGTACCGGCGACGGTACTGTGGCGAAGGGCAGAAACCG

P  F  S  P  P  P  P  F  W  R  Y  M  M  K  H  L  P
   ─────────────────────── purK ───────────────────┘

GTTCCAGTTCAATCCAAGGCGCTTTCGGGCCAGGATTCGCTACTCTCCATCGTACAGATGCCAGCGGGTA
+----+----+----+----+----+----+----+----+----+----+----+----+----+----+ 1820
CAAGGTCAAGTTAGGTTCCGCGAAAGCCCGGTCCTAAGCGATGAGAGGTAGCATGTCTACGGTCGCCCAT

TTCCCGTCGGCACTCTCGCCATCGGCCGTGCAGGCGCGGTCAATGCCGCCCTTCTCGCCGCCGCCGTTCT
+----+----+----+----+----+----+----+----+----+----+----+----+----+----+ 1890
AAGGGCAGCCGTGAGAGCGGTAGCCGGCACGTCCGCGCCAGTTACGGCGGGAAGAGCGGCGGCGGCAAGA

GGCGCTATATGATGAAGCACTTGCCGCCCGTCTTGATGAATGGCGCAAGGCGCAGACCGAAAGCGTTGCA
+----+----+----+----+----+----+----+----+----+----+----+----+----+----+ 1960
CCGCGATATACTACTTCGTGAACGGCGGGCAGAACTACTTACCGCGTTCCGCGTCTGGCTTTCGCAACGT

GAACGCCCCTCGAACGAAGCCTGATCCGGCGAGGTAGAAAATGGACAAGACATCTCTCAAGCCCGGCTCC
+----+----+----+----+----+----+----+----+----+----+----+----+----+----+ 2030
CTTGCGGGGAGCTTGCTTCGGACTAGGCCGCTCCATCTTTTACCTGTTCTGTAGAGAGTTCGGGCCGAGG
```

Fig. 3 (e)

```
ACCATCGGCATTATCGGCCGATTGGGAAACCATGCACCATGCAGCCGACACATTGGAGGCGCTCGGCATC
----+----|----+----|----+----|----+----|----+----|----+----|----+----|----+ 2100
TGGTAGCCGTAATAGCCGGCTAACCCTTTGGTACGTGGTACGTCGGCTGTGTAACCTCCGCGAGCCGTAG

Nco I
                       |
TCCTTCGACGCACGGATCGTTTCCGCCCATCGCACCCCTGACAGGCTGGTCGCCTTCGCCAAGGGGGCGA
----+----|----+----|----+----|----+----|----+----|----+----|----+----+ 2170
AGGAAGCTGCGTGCCTAGCAAAGGCGGGTAGCGTGGGGACTGTCCGACCAGCGGAAGCGGTTCCCCCGCT

AACGGGAAGGCTTCAAGGTCATCATCGCAGGCGCCGGCCGCGCCCACCTGCCCGGCATGGCCGCTGCCAT
----+----|----+----|----+----|----+----|----+----|----+----|----+----+ 2240
TTGCCCTTCCGAAGTTCCAGTAGTAGCGTCCGCGGCCGGCGCGGGTGGACGGGCCGTACCGGCGACGGTA

GACACCGCTTCCCGTCTTTGGCGTTCCAGTTCAATCCAAGGCGCTTTCGGGCCAGGATTCGCTACTCTCC
----+----|----+----|----+----|----+----|----+----|----+----|----+----+ 2310
CTGTGGCGAAGGGCAGAAACCGCAAGGTCAAGTTAGGTTCCGCGAAAGCCCGGTCCTAAGCGATGAGAGG

ATCGTACAGATGCCAGCGGGTATTCCCGTCGGCACTCTCGCCATCGGCCGTGCAGGCGCGGTCAATGCCG
----+----|----+----|----+----|----+----|----+----|----+----|----+----+ 2380
TAGCATGTCTACGGTCGCCCATAAGGGCAGCCGTGAGAGCGGTAGCCGGCACGTCCGCGCCAGTTACGGC

CCCTTCTCGCCGCCGCCGTTCTGGCGCTATATGATGAAGCACTTGCCGCCCGTCTTGATGAATGGCGCAA
----+----|----+----|----+----|----+----|----+----|----+----|----+----+ 2450
GGGAAGAGCGGCGGCGGCAAGACCGCGATATACTACTTCGTGAACGGCGGGCAGAACTACTTACCGCGTT

GGCGCAGACCGAAAGCGTTGCAGAACGCCCCTCGAACGAAGCCTGATCCGGCGAGGTAGAAAATGGACAA
----+----|----+----|----+----|----+----|----+----|----+----|----+----+ 2520
CCGCGTCTGGCTTTCGCAACGTCTTGCGGGGAGCTTGCTTCGGACTAGGCCGCTCCATCTTTTACCTGTT

GACATCTCTCAAGCCCGGCTCCACCATCGGCATTATCGGCCGATTGGGAAACCATGCACCATGCAGCCGA
----+----|----+----|----+----|----+----|----+----|----+----|----+----+ 2590
CTGTAGAGAGTTCGGGCCGAGGTGGTAGCCGTAATAGCCGGCTAACCCTTTGGTACGTGGTACGTCGGCT
```

Fig. 3 (f)

```
                                      Nco I
                                        |
CACATTGGAGGCGCTCGGCATCTCCTTCGACGCACGGATCGTTTCCGCCCATCGCACCCCTGACAGGCTG
----+----+----+----+----+----+----+----+----+----+----+----+----+----+ 2660
GTGTAACCTCCGCGAGCCGTAGAGGAAGCTGCGTGCCTAGCAAAGGCGGGTAGCGTGGGGACTGTCCGAC

GTCGCCTTCGCCAAGGGGGCGAAACGGGAAGGCTTCAAGGTCATCATCGCAGGCGCCGGCCGCGCCCACC
----+----+----+----+----+----+----+----+----+----+----+----+----+----+ 2730
CAGCGGAAGCGGTTCCCCCGCTTTGCCCTTCCGAAGTTCCAGTAGTAGCGTCCGCGGCCGGCGCGGGTGG

TGCCCGGCATGGCCGCTGCCATGACACCGCTTCCCGTCTTTGGCGTTCCAGTTCAATCCAAGGCGCTTTC
----+----+----+----+----+----+----+----+----+----+----+----+----+----+ 2800
ACGGGCCGTACCGGCGACGGTACTGTGGCGAAGGGCAGAAACCGCAAGGTCAAGTTAGGTTCCGCGAAAG

GGGCCAGGATTCGCTACTCTCCATCGTACAGATGCCAGCGGGTATTCCCGTCGGCACTCTCGCCATCGGC
----+----+----+----+----+----+----+----+----+----+----+----+----+----+ 2870
CCCGGTCCTAAGCGATGAGAGGTAGCATGTCTACGGTCGCCCATAAGGGCAGCCGTGAGAGCGGTAGCCG

CGTGCAGGCGCGGTCAATGCCGCCCTTCTCGCCGCCGCCGTTCTGGCGCTATATGATGAAGCACTTGCCG
----+----+----+----+----+----+----+----+----+----+----+----+----+----+ 2940
GCACGTCCGCGCCAGTTACGGCGGGAAGAGCGGCGGCGGCAAGACCGCGATATACTACTTCGTGAACGGC

CCCGTCTTGATGAATGGCGCAAGGCGCAGACCGAAAGCGTTGCAGAACGCCCCTCGAACGAAGCCTGATC
----+----+----+----+----+----+----+----+----+----+----+----+----+----+ 3010
GGGCAGAACTACTTACCGCGTTCCGCGTCTGGCTTTCGCAACGTCTTGCGGGGAGCTTGCTTCGGACTAG

CGGCGAGGTAGAAAATGGACAAGACATCTCTCAAGCCCGGCTCCACCATCGGCATTATCGGCCGATTGGG
----+----+----+----+----+----+----+----+----+----+----+----+----+----+ 3080
GCCGCTCCATCTTTTACCTGTTCTGTAGAGAGTTCGGGCCGAGGTGGTAGCCGTAATAGCCGGCTAACCC

Nco I
                                        |
AAACCATGCACCATGCAGCCGACACATTGGAGGCGCTCGGCATCTCCTTCGACGCACGGATCGTTTCCGC
----+----+----+----+----+----+----+----+----+----+----+----+----+----+ 3150
TTTGGTACGTGGTACGTCGGCTGTGTAACCTCCGCGAGCCGTAGAGGAAGCTGCGTGCCTAGCAAAGGCG
```

Fig. 3 (g)

```
CCATCGCACCCCTGACAGGCTGGTCGCCTTCGCCAAGGGGGCGAAACGGGAAGGCTTCAAGGTCATCATC
----+----|----+----|----+----|----+----|----+----|----+----|----+----| 3220
GGTAGCGTGGGGACTGTCCGACCAGCGGAAGCGGTTCCCCCGCTTTGCCCTTCCGAAGTTCCAGTAGTAG

GCAGGCGCCGGCCGCGCCCACCTGCCCGGCATGGCCGCTGCCATGACACCGCTTCCCGTCTTTGGCGTTC
----+----|----+----|----+----|----+----|----+----|----+----|----+----| 3290
CGTCCGCGGCCGGCGCGGGTGGACGGGCCGTACCGGCGACGGTACTGTGGCGAAGGGCAGAAACCGCAAG

CAGTTCAATCCAAGGCGCTTTCGGGCCAGGATTCGCTACTCTCCATCGTACAGATGCCAGCGGGTATTCC
----+----|----+----|----+----|----+----|----+----|----+----|----+----| 3360
GTCAAGTTAGGTTCCGCGAAAGCCCGGTCCTAAGCGATGAGAGGTAGCATGTCTACGGTCGCCCATAAGG

CGTCGGCACTCTCGCCATCGGCCGTGCAGGCGCGGTCAATGCCGCCCTTCTCGCCGCCGCCGTTCTGGCG
----+----|----+----|----+----|----+----|----+----|----+----|----+----| 3430
GCAGCCGTGAGAGCGGTAGCCGGCACGTCCGCGCCAGTTACGGCGGGAAGAGCGGCGGCGGCAAGACCGC

CTATATGATGAAGCACTTGCCGCCCGTCTTGATGAATGGCGCAAGGCGCAGACCGAAAGCGTTGCAGAAC
----+----|----+----|----+----|----+----|----+----|----+----|----+----| 3500
GATATACTACTTCGTGAACGGCGGGCAGAACTACTTACCGCGTTCCGCGTCTGGCTTTCGCAACGTCTTG

GCCCCTCGAACGAAGCCTGATCCGGCGAGGTAGAAAATGGACAAGACATCTCTCAAGCCCGGCTCCACCA
----+----|----+----|----+----|----+----|----+----|----+----|----+----| 3570
CGGGGAGCTTGCTTCGGACTAGGCCGCTCCATCTTTTACCTGTTCTGTAGAGAGTTCGGGCCGAGGTGGT

|Nco I
                                  |
TCGGCATTATCGGCCGATTGGGAAACCATGCACCATGCAGCCGACACATTGGAGGCGCTCGGCATCTCCT
----+----|----+----|----+----|----+----|----+----|----+----|----+----| 3640
AGCCGTAATAGCCGGCTAACCCTTTGGTACGTGGTACGTCGGCTGTGTAACCTCCGCGAGCCGTAGAGGA

TCGACGCACGGATCGTTTCCGCCCATCGCACCCCTGACAGGCTGGTCGCCTTCGCCAAGGGGGCGAAACG
----+----|----+----|----+----|----+----|----+----|----+----|----+----| 3710
AGCTGCGTGCCTAGCAAAGGCGGGTAGCGTGGGGACTGTCCGACCAGCGGAAGCGGTTCCCCCGCTTTGC

GGAAGGCTTCAAGGTCATCATCGCAGGCGCCGGCCGCGCCCACCTGCCCGGCATGGCCGCTGCCATGACA
----+----|----+----|----+----|----+----|----+----|----+----|----+----| 3780
CCTTCCGAAGTTCCAGTAGTAGCGTCCGCGGCCGGCGCGGGTGGACGGGCCGTACCGGCGACGGTACTGT
```

Fig. 3 (h)

```
CCGCTTCCCGTCTTTGGCGTTCCAGTTCAATCCAAGGCGCTTTCGGGCCAGGATTCGCTACTCTCCATCG
━━━━┿━━━━┿━━━━┿━━━━┿━━━━┿━━━━┿━━━━┿━━━━┿━━━━┿━━━━┿━━━━┿━━━━┿━━━━┿━━━━+ 3850
GGCGAAGGGCAGAAACCGCAAGGTCAAGTTAGGTTCCGCGAAAGCCCGGTCCTAAGCGATGAGAGGTAGC

TACAGATGCCAGCGGGTATTCCCGTCGGCACTC
━━━━┿━━━━┿━━━━┿━━━━┿━━━━┿━━━━┿━━▶ 3883
ATGTCTACGGTCGCCCATAAGGGCAGCCGTGAG
```

Fig. 3 (i)

MUTANTS OF *BRUCELLA MELITENSIS*

This application is a continuation-in-part of U. S. Pat. application No. 08/334,129, filed Nov. 4, 1994, which is now abandoned.

FIELD OF THE INVENTION

This invention relates to mutants of *Brucella melitensis* for use as a vaccine.

BACKGROUND OF THE INVENTION

Brucella infects a significant number of people and domestic herds in developing nations and domestic and wild animals of the United States. Brucellosis in man may be caused by a number of strains of Brucella including *B. abortus* (cattle), *B. suis* (hogs), *B. rangiferi* (caribou), *B. melitensis* (sheep and goats) and *B. canis* (dogs). The disease is acquired by exposure to secretions and excretions of infected animals and by ingestion of milk or milk products from infected animals. The current live-attenuated vaccine strains for animals cause disease in humans, abortions in adult animals and complicates immunological screening for infected animals, since they stimulate production of antibodies to lippopolysaccharide (LPS) which is detected in the milk and serum of vaccinated animals. These antibodies are detected in serological tests used to screen milk and meat for Brucella.

Two approved live-attenuated Brucella vaccines are currently used to vaccinate animals. Strain 19 is currently used to vaccinate animals against *B. abortus* infections. This live-attenuated strain has several characteristics that make it undesirable as a human vaccine. The attenuating mutation in this strain is unknown; it sero-converts vaccinated individuals making differentiation of infected and vaccinated individuals difficult and causes significant disease in humans. Another live-attenuated veterinary vaccine *B. melitensis* strain, REV1 has the same limitations as Strain 19. Recently, a rough mutation of *B. abortus*, RB51, has been tested and found to be safe and protective in a number of different animal models. This rough live-attenuated strain was derived from a rifampin resistant strain and the mutation causing the rough phenotype and attenuation is not identified. Although RB51 does not stimulate the production of antibodies to LPS, it stimulates portective immunity in animals and does not cause abortions in vaccinated animals. Since the nature of the genetic defect causing the rough phenotype is not known, it is not possible to predictably make a vaccine under appropriate manufacturing procedures for human use. Brucella strains have not been used as live-attenuated vaccine carriers for recombinant proteins.

Brucella also presents a potential biowarfare threat for military personnel. Multiple antibiotic resistant strains of Brucella have been constructed by others and pose a significant threat to the morbidity and mortality of infected personnel.

O'Callaghan (*Infection and Immunity*, Vol. 56, No. 2, pp 419–423 (1988)) describes deletion mutants of Salmonella having purE and purA deletions. Neither was effective as an oral vaccine. Hence, O'Callaghan would direct interest of those of ordinary skill from the purE deletion mutants for use as vaccines.

Houng, et al, (*Abstracts of the 94th General Meeting of ASM*, page 133, Abstract D-208) teaches that the writers identified purEK genes and identified two polypeptides that are products of these genes. However, they do not teach any particular mutant, nor do they teach how to make any mutant. Furthermore, they do not suggest any particular use for any mutant. (Taken with O'Callaghan, one of ordinary skill would not be directed to use such a mutant for a vaccine.)

Smith and Heffron (*Infection and Immunity*, Vol. 55, No. 11, pp 2774–2776 (1987)) teaches transposon Tn5 mutagenesis of Brucella abortus involving transposon Tn5. His construct is not made by the method of the invention. The instantly claimed invention does not involve introduction of Tn5 or Tn5 lac into a DNA sequence. Adams, in *Advances in Brucellosis Research*, Chapter 17, pages 250 to 276 (1990) suggests that Tn10 mutagenesis may be used to identify genes encoding virulence factors for adherence, invasion and intracellular survival, and that this method might be applicable to study of Brucella. He suggests no particular mutation. The instantly claimed invention was not suggested by Adams and was not made by the methods of Adams. Stocker in U.S. Pat. No. 4,735,801, suggests similar means of making mutants of Salmonella strains. Stocker introduced one or more modifications in biosynthetic pathways for products unlikely to be found in the disease susceptible host. Auxotrophic mutations are produced in one or more pathways by deletion or inversion of the target gene. These mutations can not be repaired by a single step and are referred to as non-reverting. In this patent he identifies aro, dap, pab and pur target genes for the construction of live vaccine strains. The pur gene targets claimed were those biosynthetic genes involved in the conversion of inosine monophosphate to adenine. He does not suggest the deletion mutants of the invention.

SUMMARY OF THE INVENTION

It is the purpose of this invention to provide a safe, effective vaccine to protect against brucellosis in man and animals. Live vaccines are provided and methods for preparing live vaccine for protection of a host from infection with Brucella species. The vaccines are prepared by isolating the Brucella genes complementing mutations in the purEK genes of *Escherichia coli*, physically mapping, determining the DNA sequence, constructing a defined deletion mutation by polynucleotide chain reaction (PCR), introducing a selectable marker into the deletion, and then selecting a purE mutant in Brucella arising by allelic exchange. The resulting Brucella require purines for growth because they lack the purE gene product that is required for the carboxylation of 5'-phosphoribosyl-5-aminoimidazole. Since the purE mutation occurs before the synthesis of inosine monophosphate (IMP), these mutants can grow when supplied with exogenous adenine, hypoxanthine or guanine. In contrast, purA or purB mutants which block bio-synthetic steps after IMP can grow only when exogenous adenine is supplied. Unlike purE mutants of Salmonella, purE mutants of Brucella are substantially reduced in virulence and stimulate protective immunity from infection with wild-type Brucella. In contrast to purA or purB mutants of Salmonella, purE mutants of Brucella are capable of systemic spread from mucosal tissues. Therefore, purE mutants of Brucella are capable of stimulating mucosal, systemic and cellular immune responses to itself as well as to heterologous antigens expressed by Brucella.

The genetically engineered organisms of the invention grow at a significantly reduced rate when compared with the wild-type and are unable to escape the phagolysosome in human monocytes in cell culture. Hence, the organisms are useful for providing a safe, effective live vaccine carrier strain for production of antigen-specific cytotoxic T-cells and memory T-helper cells with specific reactivity for recombinant Brucella or non-brucella peptides.

The purE deletion mutant of *B. melitensis* is designed to be a live-attenuated vaccine for prevention of brucellosis. Since this strain remains as infectious as the wild-type 16M *B. melitensis*, and persists with reduced growth in human monocytes, it will deliver a high antigenic load at target mucosal surfaces and induce both cellular and humoral responses to the bacteria and any recombinant gene expressed by the bacteria. In addition, escape from the phagolysosome increases the processing and presentation of antigens by HLA class 1 proteins. These factors indicate methods of the invention would favor the production of antigen-specific cytotoxic T cells. The genetically engineered bacteria may be administered by method usual in the art, including injection. Methods that would avoid necessity of injection should be considered. The attenuated organisms may, for example, be administered orally in syrup, capsules, in carbonated buffers or nasally via a mist.

BRIEF DESCRIPTION OF THE FIGURES

FIG. 2 shows the pURE3H: 7.9 kb HindIII insert of *Brucella melitensis* in pHC79.

Figure 1:
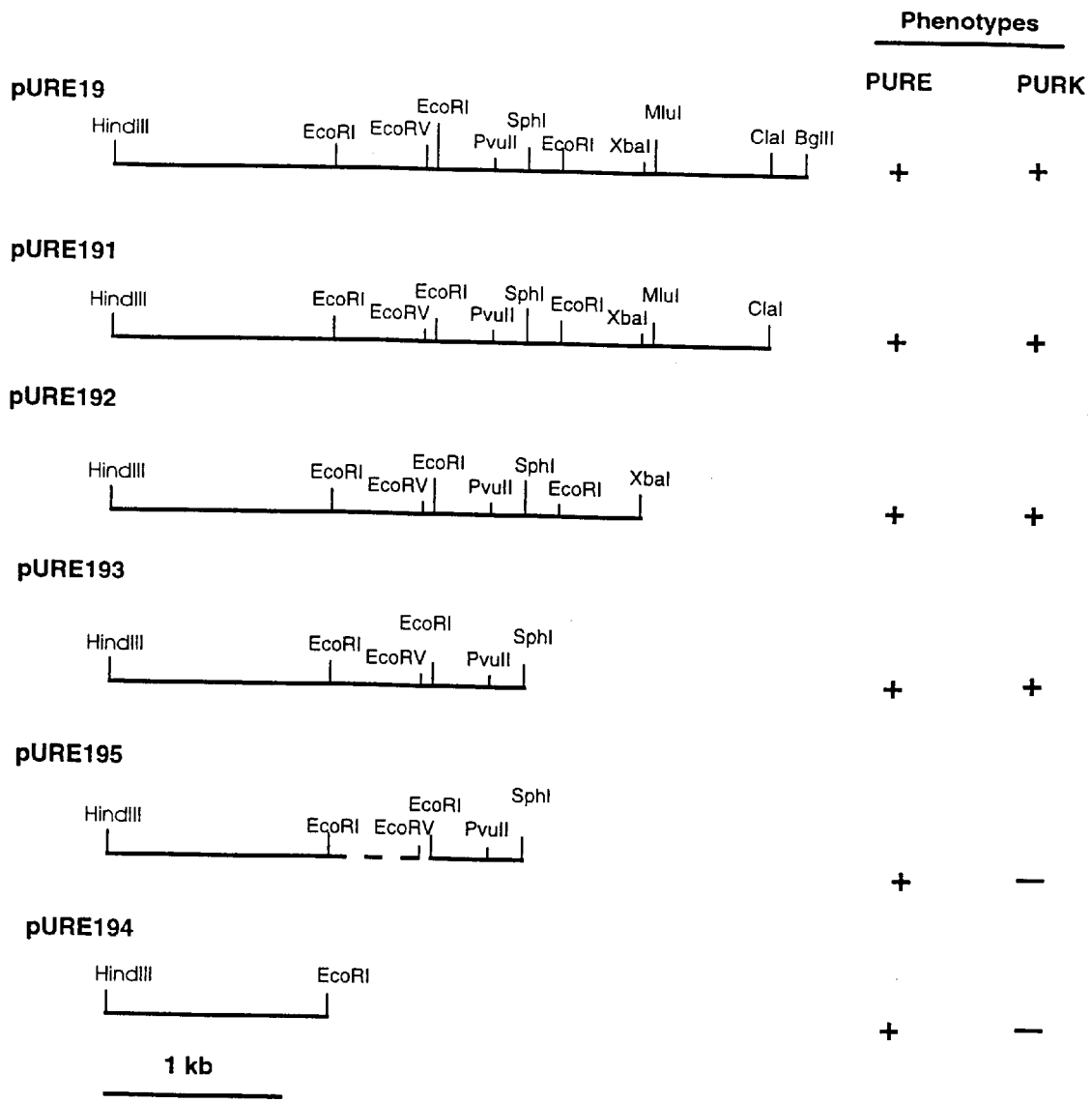
FIG. 1 shows the purE coding region of *Brucella melitensis*.

FIG, 3 identifies purEK as was produced in accord with the deletions.

DETAILED DESCRIPTION OF THE INVENTION

This invention provides attenuated *B. melitensis*. The attenuated, genetically engineered organisms provide active immunity against Brucellosis species. The reduced growth rate of Brucella in the phagolysosome of human monocytes grown in cell culture renders the purE mutant a useful agent for use as a live, attenuated vaccine.

The purEK operon and purE gene have not previously been described for Brucella. The organism wherein the purE gene has been deleted from Brucella purE mutant is the first genetically characterized mutant of Brucella that fails to replicate in human monocytes. Previously, no genetically defined mutants of Brucella have been successfully developed for use as live, attenuated Brucella vaccines or as vaccine carriers. The purE mutant may also be a safe and effective live-vaccine carrier strain for the production of non-Brucella antigen-specific cytotoxic T-cells, and memory T-helper cells with specific reactivity for recombinant Brucella or non-Brucella peptides. A purE deletion mutant of *B. melitensis* should be a safe and effective live-attenuated vaccine for the prevention of brucellosis in humans and in animals when used alone or in combination with other deletion mutations in brucella genes such as aro, rfb, htr, rec or global regulatory genes. The purE deletion mutant can be used as a live-attenuated vaccine carrier for the stimulation of immune responses to bacterial, viral and fungal pathogens or any other antigens of interest that can be expressed by the carrier organism. It would be particularly appropriate to vaccinate dairy workers and other animal handlers and packing house workers.

The attenuated vaccine would also be useful for administration to lower animals that are likely to be infected with Brucella species. The administration of vaccine to military personnel that might be subjected to the organisms during biological warfare would also be appropriate. Finally, vaccination against brucellosis of travelers who will be likely to ingest unpasteurized milk should be considered.

The purEK operon of *Brucella melitensis* strain 16M was isolated and sequenced by complementing a purE::Tn10 mutation in *Escherichia coli*. Based upon the DNA sequence of this operon, deletions in the open reading frames (ORFs) that correspond to the purK and purE genes were defined. Deletion of the internal EcoRI fragment resulted in *E. coli* carrying the purE::Tn10 mutation growing on minimal media only in the presence of 5% $CO_2$, confirming the identification of the purk ORF. A deletion mutation of the purE ORF was made by PCR amplification of pURE194 with oligonuceotides designed with an unique BglII restriction endonuclease site on the 5' ends. These primers produced a plasmid pURE197 that lacked bp 435-713 of the purE ORF. *E. coli* purE::Tn10 carrying this plasmid grew only on minimal plates supplemented with purines. A Bam HI fragment carrying a kanamycin resistance cassette was cloned into the BglII site of pURE197 to make pURE198. Gene exchange in *B. melitensis* was accomplished by electroporation of pURE198 into *B. melitensis strain* 16M. The plasmid vector does not replicate in *B. melitensis* and kanamycin resistant colonies arise following single or double cross-over events. Double cross-over events between the wild-type chromosomal copy of the purEK operon and the purEKmK gene on the plasmid results in a *B. melitensis* that is KMr, AMPs and PurE-.

METHODS AND MATERIALS

A HindIII genomic library of *B. melitensis* was screened for transformants that complemented purE::Tn10 mutation in *Escherichia coli* strain RR1. A plasmid carrying *19* kilobases of *B. melitensis* DNA was isolated from *E. coli* growing on minimal media. A subcloned fragment of 3.9 kb (pURE193) that complemented the purE::Tn10 mutation in *E. coli* was isolated from the original DNA and sequenced (GenBank accession number U10241). Two open reading frames encoding for two polypeptides of 17 kd and 40 kd were found. A search of the DNA and protein databases showed 64.5% homology of the 17 kd peptide with purE and 41.5% homology of the 40 kd peptide with purK of *E. coli*. Deletion mutations of the putative purE and purK genes were made in *B. Melitensis* strain 16M by gene replacement. Deletion of the purK locus produced a strain of Brucella that grew faster in 5% $CO_2$ than in air, consistent with a PurK-phenotype. Deletion of the purE locus produced a Brucella strain that requires purines for growth on M9 minimal media, consistent with a purE mutation. A deletion mutation within purE was made by PCR amplification. These primers produced a fragment that deleted bp 435–713 of the pURE193. Next, a BamHI fragment carrying a kanamycin resistance cassette was cloned into an internal BglII site of the deletion mutant. The resulting plasmid was electro-porated into *B. Melitensis* strain 16M. DNA hybridization analysis of DNA isolated from two purE strains confirmed that the wild-type gene was replaced by a single copy of the purE deletion mutation carrying the kanamycin resistance cassette. Isolated human monocytes with wild-type 16 M and with purE- *B. Melitensis* strains BM198-7 and BM201-1 were infected. While the parent 16M strain increased over two logs in 72 hours, the purE mutants decreased by 2 logs. The purE mutation did not reduce the number of bacteria recovered one hour after infection of the monocytes when compared with wild-type 16M. These results show that the purE mutation reduces the capacity of *B. Melitensis* to grow within human monocytes without altering its capacity to infect the host's cells.

FIG. 1 shows the purE coding region of *Brucella melitensis*. Only the inserted portions of these recombinant plasmids are shown. Plasmid phenotypes were determined by complementation tests using *E. coli* RR1 purE::Tn10 mutant as the cloning host. Plasmid pURE19 was constructed by ligating the 4.0 kb HindIII-BglII fragment of pURE3H into pUC19, which was previously digested with HindIII and BamHI. Plasmid pURE191 and pURE192 were constructed by subcloning the 3.8 kb HindII-ClaI and the 3.3 kb HindIII-XbaI fragments of pUREl9 into the corresponding sites of pACYC184 vector. Plasmid pURE193 was constructed by subcloning the 2.2 kb HindIII-SphI fragment of pUREl9 into its corresponding sites of pBR328.

FIG. 2 shows pURE3H wherein the 7.0 kb HindIII of *B. melitensis* has been inserted into pHC79. to provide the 13.4 kb pURE3H.

The DNA containing the purE mutation contains the following sequence:

```
GTGAGCGGAT AACAATTTCA CACAGGAAAC AGCTATGACC ATGATTACGC CAAGCTTCAG
GAAATGGAAG ATCAGGTCAT TCCTGACATC ATTGCCTGAA CATTCAAGAA CACTATAGGG
AAGAGCCGGG GTTCGCTGCT TGTCTTTTCA AGACCTTCCT CATGCCAACC GAAAAGCCAA
GCAGGAAAGA CCGATGAGCG TTGATGTCGC CATTATCATG GGAAGCCAGT CCGATTGGGA
AACCATGCAC CATGCAGCCG ACACATTGGA GGCGCTCGGC ATCTCCTTCG ACGCACGGAT
CGTTTCCGCC CATCGCACCC CTGACAGGCT GGTCGCCTTC GCCAAGGGGG CGAAACGGGA
AGGCTTCAAG GTCATCATCG CAGGCGCCGG CCGCGCCCAC CTGCCCGGCA TGGCCGCTGC
CATGACACCG CTTCCCGTCT TTGGCGTTCC AGTTCAATCC AAGGCGCTTT CGGGCCAGGA
TTCGCTACTC TCCATCGTAC AGATGCCAGC GGGTATTCCC GTCGGCACTC TCGCCATCGG
CCGTGCAGGC GCGGTCAATG CCGCCCTTCT CGCCGCCGCC GTTCTGGCGC TATATGATGA
AGCACTTGCC GCCCGTCTTG ATGAATGGCG CAAGGCGCAG ACCGAAAGCG TTGCAGAACG
CCCCTCGAAC GAAGCCTGAT CCGGCGAGGT AGAAAATGGA CAAGACATCT CTCAAGCCCG
GCTCCACCAT CGGCATTATC GGCGGGGGCC AGCTTGGCGT ATGCTCGCCA TGGCAGCGGC
GCGCTTCGGT TATGAAACCA TAATCCTTGA GCCGCACGCG GTTGCCCGGC AGCACAGGTT
GCCAATCGCC AGATTGTCGC CGCCTATGAT GACCCGAAGC GCTGGCCGAA ACTTGCCGCC
GCTTCCGACG TCATCACCTA TGAATTTGAA AATGTGCCAA TCAGCGCCGC CGACAAGCTG
GCTGAAACGG CGCTTGTTCT GCCCCCGCCC GCCGCACTGG AAATCTCTCA GGACCGCTTC
ACAGAAAAGC AGTTTCTCAA CGAAAGCGGC ATTGAAACCG CGCCCTGGCG GCTCGTGGAT
GACGAGGAAA CGCTCATCGC CGCGCTCGGC ACTTGGGCGG GCGTGGCATC CTCAAGATCG
GCGTCTGGGT TATGACGGCA AGGGGCAGGT GCGCCTTGCC TCCCTCGATG AAACCCAGGC
CTGCAACGCT TTTGCAGCCA TCAACAAGGC GCCTGCGATT CTCGAAGGCT TCGTGGAATT
CGAGCGCGAA GTCTCCGTCA TCGCCGCGCG CGATCGCAGC GGCAATGTCG CCATCTTCGA
TCTTGCGGAA AACGTCCACA AGGATGGCAT TCTCGCCACG TCCACAGTGC CTGCCGCGAT
CAGCGTACAG ACGGCAGAAG CCGCGCGCAC AGCCGCCGAA AAACTGTTGC ACGCGCTGGA
CTATGTCGGT GTGCTGGGGC TTGAATTCTT CGTGCTGAAG GACGGCACGC TGCTCGCCAA
TGAATTTGCC CCGCGTGTGC ATAATTCGGG CCACTGGACG GAAGCAGCCT GCGCCATTTC
CCAATTTGAG CAGCATATCC GCGCTGTGGC GGGACTGCCG CTCGGCAATA CGGATCGCCA
TAGCGACTGT GTGATGGAAA ACCTGATTGG CGACGATATC GAAAAGGTTC CGGCGATTCT
CTGCGAGAAG AACGCCGTGC TGCATCTTTA CGGTAAAAAG GAAGCTCGCG CGGGCCGGAA
AATAGGCCAT GTGACCCGCA TAAAGCCCCG CACAATTTAA GCTGCGCCGG GAATCTGCAC
GATTCCCGGC CCTTCCTGGC CGCCCGCCAA GAAATTCGGG GCCTCGGACC CTGAATCTGC
GGCGCGGGAG TTGACATTTG CCTGAAACCT TGTGTATTTC GGCCAACTTC GGCACCTGAC
``` which is designated as Sequence #1 herein and has been deposited in the GenBank wherein the accession number U10241 has been assigned.

The 17 kD and 40 kD polypeptides encoded by Sequence #1 are:

```
Met Ser Val Asp Val Ala Ile Ile Met Gly Ser Gln Ser Asp Trp Glu   (Sequence #2)
 1               5                  10                 15

Thr Met His His Ala Ala Asp Thr Leu Glu Ala Leu Gly Ile Ser Phe
            20                  25                 30

Asp Ala Arg Ile Val Ser Ala His Arg Thr Pro Asp Arg Leu Val Ala
            35                  40                 45

Phe Ala Lys Gly Ala Lys Arg Glu Gly Phe Lys Val Ile Ile Ala Gly
      50                  55                  60

Ala Gly Arg Ala His Leu Pro Gly Met Ala Ala Met Pro Leu
 65                  70                  75              80

Pro Val Phe Gly Val Pro Val Gln Ser Lys Ala Leu Ser Gly Gln Asp
                    85                  90                  95

Ser Leu Leu Ser Ile Val Gln Met Pro Ala Gly Ile Pro Val Gly Thr
            100                 105                 110

Leu Ala Ile Gly Arg Ala Gly Ala Val Asn Ala Ala Leu Leu Ala Ala
            115                 120                 125

Ala Val Leu Ala Leu Tyr Asp Glu Ala Leu Ala Ala Arg Leu Asp Glu
      130                 135                 140

Trp Arg Lys Ala Gln Thr Glu Ser Val Ala Glu Arg Pro Ser Asn Glu
145                 150                 155                 160

Ala
``` and

-continued

```
Met Leu Ala Met Ala Ala Ala Arg Phe Gly Tyr Glu Thr Ile Ile Leu    (Sequence #3)
 1           5               10              15

Glu Pro His Ala Val Ala Arg Gln His Arg Leu Pro Ile Ala Arg Leu
            20              25              30

Ser Pro Pro Met Met Thr Arg Ser Ala Gly Arg Asn Leu Pro Pro Leu
            35              40              45

Pro Thr Ser Ser Pro Met Asn Leu Lys Met Cys Gln Ser Ala Pro Pro
     50              55              60

Thr Ser Trp Leu Lys Arg Arg Leu Phe Cys Pro Arg Pro Pro His Trp
 65              70              75              80

Lys Ser Leu Arg Thr Ala Ser Gln Lys Ser Ser Phe Ser Thr Lys Ala
                 85              90              95

Ala Leu Lys Pro Arg Pro Gly Gly Ser Trp Met Thr Arg Lys Arg Ser
            100             105             110

Ser Pro Arg Ser Ala Leu Gly Arg Ala Trp His Pro Gln Asp Arg Arg
            115             120             125

Leu Gly Tyr Asp Gly Lys Gly Gln Val Arg Leu Ala Ser Leu Asp Glu
            130             135             140

Thr Gln Ala Cys Asn Ala Phe Ala Ala Ile Asn Lys Ala Pro Ala Ile
145             150             155             160

Leu Glu Gly Phe Val Glu Phe Glu Arg Glu Val Ser Val Ile Ala Ala
                165             170             175

Arg Asp Arg Ser Gly Asn Val Ala Ile Phe Asp Leu Ala Glu Asn Val
            180             185             190

His Lys Asp Gly Ile Leu Ala Thr Ser Thr Val Pro Ala Ala Ile Ser
            195             200             205

Val Gln Thr Ala Glu Ala Ala Arg Thr Ala Ala Glu Lys Leu Leu His
    210             215             220

Ala Leu Asp Tyr Val Gly Val Leu Gly Leu Glu Phe Phe Val Leu Lys
225             230             235             240

Asp Gly Thr Leu Leu Ala Asn Glu Phe Ala Pro Arg Val His Asn Ser
            245             250             255

Gly His Trp Thr Glu Ala Ala Cys Ala Ile Ser Gln Phe Glu Gln His
            260             265             270

Ile Arg Ala Val Ala Gly Leu Pro Leu Gly Asn Thr Asp Arg His Ser
    275             280             285

Asp Cys Val Met Glu Asn Leu Ile Gly Asp Asp Ile Glu Lys Val Pro
    290             295             300

Ala Ile Leu Cys Glu Lys Asn Ala Val Leu His Leu Tyr Gly Lys Lys
305             310             315             320

Glu Ala Arg Ala Gly Arg Lys Ile Gly His Val Thr Arg Ile Lys Pro
            325             330             335

Arg Thr Ile
```

Adams (cited supra) outlines a systematic approach to the valuation of the safety and efficacy of candiate Brucella vaccines. Appropriate vaccines are shown to have alter growth in vitro, reduced growth in macrophages, peeripheral blood monocytes or in tissue culture systems should be assayed in mice. Although the mouse model is not ideal, it is useful for deciding which candidate vaccines should be tested in the natural host. Under testing as described, B melitensus ΔpurE201 is attenuated for growth in both human and mouse macrophages. Further, pSD5, a plasmid carrying an expressed copy of the purE gene, restores the capacity of B. melitensis ΔpurE201 to grow on minimal media without exogenous purines and within human macrophages, confirming that the attnuated growth is due to the purE deletion and not due to some unknown secondary mutation. The purE mutation described was attenuated in human monocytes, in mice and in goats.

B melitensis ΔpurE201 as attenuated in the mouse was cleared from the spleens of mice by eight weeks following intraperitoneal injection. Wild-type 16M is not cleared from the spleens of mice. Table 1 shows that the ΔpurE201 is attenuated when given orally to mice. These results show that ΔpurE201 is unable to scavenge sufficient purines for persistent growth in tissues of the infected host.

TABLE I

Oral attenuation of *B meitensus* ΔpurE201
Infection of BALB/c mice after oral challenge with *B. melitensis*

| strains | Week 1 | Week 2 | Week 4 |
|---|---|---|---|
| 16M | 2/5 | 4/5 | 3/5 |
| purE201 | 0/5 | 0/5 | 0/5 |

To test the immunizing ability of ΔpurE201, BALB/c mice were injected with $10^5$ colony forming units. Rising antibody titers against Brucella LPS was shown following vaccination. The antibody induced by ΔpurE201 cross reacts with LPS prepared from *B. abortus* 2308 LPS following vaccination. It was shown that the ΔpurE201 induces protective immunity from intranasal challenge with wildtype 16M.

TEST

PROTECTION AGAINST INTRANASAL CHALLENGE

Mice were immuinized with $10^5$ *B melitensis* ΔpurE201 ip. then challenged 9 weeks later with $10^5$ 16M in harvested at 4 weeks to determine recovery of *B melitensis*. Among the nonimmunized mice, 8 of 10 were infected. Among those immunized with the mutant, only 2/10 were infected.

The study was extended with spleens being harvested at varying intervals. The mice were immunized with $10^5$ *B. melitensus* ΔpurE201 i.p, then challenged 9 weeks later with $10^4$ 16M intranasally. (See Table 2 below.)

TABLE 2

Protection against intranasal challenge.
The number showing infected spleens at various intervals is indicated.

|  | 4 weeks | 8 weeks | 13 weeks |
|---|---|---|---|
| noniminunized | 8/10 | 6/10 | 8/10 |
| purE-immunized | 2/10 | 4/10 | 4/10 |

In view of the above, it is seen that vaccines produced by the defined mutations in *E coli* with plasmids carrying the mutated Brucella genes of the invention having the defined deletions provides non-reverting deletions mutants which stimulate protective immunity.

Improved safety may be attained by introducing a second defined attenuating mutation. In addition to mutations which impair ability to synthesize purine, other mutations may be effective. Examples of other attenuating mutations used alone or in combination with the purE included deletions in the biosynthetic pathway for LPS biosynthesis producing a rough phenotype. These mutations attenuate Brucella and prevent the vaccinated animal from seroconverting to LPS the predominant antibody detected in immune surveillance of animals.

Many deletions in genes required for homologous recombination have been shown to attenuate live-bacterial vaccines. A combination purE recA mutation of Brucella can be made by making a deletion of the recA gene based upon the published DNA sequence of this gene.

Living organisms respond to stress by producing a number of proteins referred to as heat-shock proteins. Deletion of one of these genes htrA has been shown to attenuate bacteria. A combination purE htrA vaccine strain can be made based upon the published sequence of the Brucella htrA gene. In addition to the double defined deletion mutations, combinations of three or more genes may be constructed. In all cases, those strains carrying a recA mutation will have the recA deletion added last, since this mutation will prevents gene replacement by recombination. Finally, bacterial RNA polymerase uses sigma factors to initiate gene transcription. Deletion mutants in sigma factor genes can be combined with purE to produce live-attenuated genes.

Live-attenuated Brucella can be used as a vaccine vector to deliver foreign antigens. Since Brucella is a mucosal pathogen and survives within host cells it should have the capacity to stimulate mucosal, systemic and cellular immune responses to the delivered antigen. Processing and presentation of antigens via Class 1 HLA surface molecules of antigen-presenting cells may stimulate strong cytotoxic T-cell responses by both CD4 and CD8 T-cells to the target antigen.

We claim:

1. A recombinant *E. coli* containing an insert of a Brucella species coding region wherein the purE gene has been mutated, containing SEQUENCE ID NO 1, which is

```
GTGAGCGGAT AACAATTTCA CACAGGAAAC AGCTATGACC
ATGATTACGC CAAGCTTCAG GAAATGGAAG ATCAGGTCAT
TCCTGACATC ATTGCCTGAA CATTCAAGAA CACTATAGGG
AAGAGCCGGG GTTCGCTGCT TGTCTTTTCA AGACCTTCCT
CATGCCAACC GAAAAGCCAA GCAGGAAAGA CCGATGAGCG
TTGATGTCGC CATTATCATG GGAAGCCAGT CCGATTGGGA
AACCATGCAC CATGCAGCCG ACACATTGGA GGCGCTCGGC
ATCTCCTTCG ACGCACGGAT CGTTTCCGCC CATCGCACCC
CTGACAGGCT GGTCGCCTTC GCCAAGGGGG CGAAACGGGA
AGGCTTCAAG GTCATCATCG CAGGCGCCGG CCGCGCCCAC
CTGCCCGGCA TGGCCGCTGC CATGACACCG CTTCCCGTCT
TTGGCGTTCC AGTTCAATCC AAGGCGCTTT CGGGCCAGGA
TTCGCTACTC TCCATCGTAC AGATGCCAGC GGGTATTCCC
GTCGGCACTC TCGCCATCGG CCGTGCAGGC GCGGTCAATG
CCGCCCTTCT CGCCGCCGCC GTTCTGGCGC TATATGATGA
AGCACTTGCC GCCCGTCTTG ATGAATGGCG CAAGGCGCAG
ACCGAAAGCG TTGCAGAACG CCCCTCGAAC GAAGCCTGAT
CCGGCGAGGT AGAAAATGGA CAAGACATCT CTCAAGCCCG
GCTCCACCAT CGGCATTATC GGCGGGGGCC AGCTTGGCGT
ATGCTCGCCA TGGCAGCGGC GCGCTTCGGT TATGAAACCA
TAATCCTTGA GCCGCACGCG GTTGCCCGGC AGCACAGGTT
GCCAATCGCC AGATTGTCGC CGCCTATGAT GACCCGAAGC
GCTGGCCGAA ACTTGCCGCC GCTTCCGACG TCATCACCTA
TGAATTTGAA AATGTGCCAG TCAGCGCCGC CGACAAGCTG
GCTGAAACGG CGCTTGTTCT GCCCCCGCCC GCCGCACTGG
AAATCTCTCA GGACCGCTTC ACAGAAAAGC AGTTTCTCAA
CGAAAGCGGC ATTGAAACCG CGCCCTGGCG GCTCGTGGAT
GACGAGGAAA CGCTCATCGC CGCGCTCGGC ACTTGGGCGG
GCGTGGCATC CTCAAGATCG GCGTCTGGGT TATGACGGCA
AGGGGCAGGT GCGCCTTGCC TCCCTCGATG AAACCCAGGC
CTGCAACGCT TTTGCAGCCA TCAACAAGGC GCCTGCGATT
CTCGAAGGCT TCGTGGAATT CGAGCGCGAA GTCTCCGTCA
TCGCCGCGCG CGATCGCAGC GGCAATGTCG CCATCTTCGA
TCTTGCGGAA AACGTCCACA AGGATGGCAT TCTCGCCACG
TCCACAGTGC CTGCCGCGAT CAGCGTACAG ACGGCAGAAG
CCGCGCGCAC AGCCGCCGAA AAACTGTTGC ACGCGCTGGA
CTATGTCGGT GTGCTGGGGC TTGAATTCTT CGTGCTGAAG
GACGGCACGC TGCTCGCCAA TGAATTTGCC CCGCGTGTGC
ATAATTCGGG CCACTGGACG GAAGCAGCCT GCGCCATTTC
CCAATTTGAG CAGCATATCC GCGCTGTGGC GGGACTGCCG
CTCGGCAATA CGGATCGCCA TAGCGACTGT GTGATGGAAA
ACCTGATTGG CGACGATATC GAAAAGGTTC CGGCGATTCT
CTGCGAGAAG AACGCCGTGC TGCATCTTTA CGGTAAAAAG
GAAGCTCGCG CGGGCCGGAA AATAGGCCAT GTGACCCGCA
TAAAGCCCCG CACAATTTAA GCTGCGCCGG GAATCTGCAC
GATTCCCGGC CCTTCCTGGC CGCCCGCCAA GAAATTCGGG
GCCTCGGACC CTGAATCTGC GGCGCGGGAG TTGACATTTG
CCTGAAACCT TGTGTATTTC GGCCAACTTC GGCACCTGAC.
```

2. A composition of matter containing an immunologically effective amount of Brucella having a purE mutation of SEQUENCE ID NO 1, said Brucella organism being in a pharmaceutically acceptable carrier.

3. A composition of claim 2 wherein the pharmaceutical carrier is a syrup.

4. A composition of claim 2 in a capsule.

5. A method of immunizing a mammal against brucellosis comprising administration of an immunologically effective amount of a composition of claim 2 to provide protective immune response against infection with brucellosis organisms.

6. A method of claim 5 wherein the composition is administered in capsule form.

7. A method of claim 5 wherein the composition is administered as a syrup.

8. A method of claim 5 wherein the antigenic composition is administered as a mist.

9. A method of claim 5 wherein the carrier is a carbonated buffer.

* * * * *